US012778609B2

(12) United States Patent
Skujins et al.

(10) Patent No.: US 12,778,609 B2
(45) Date of Patent: *Nov. 3, 2026

(54) ASPIRATION PULSATOR

(71) Applicant: Covidien LP, Mansfield, MA (US)

(72) Inventors: Peter Skujins, Menifee, CA (US); Brad L. Jackson, San Diego, CA (US); Xiaodong Ma, Acton, MA (US)

(73) Assignee: Covidien LP, Mansfield, MA (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/598,697

(22) Filed: Mar. 7, 2024

(65) Prior Publication Data

US 2024/0206893 A1 Jun. 27, 2024

Related U.S. Application Data

(63) Continuation of application No. 17/100,360, filed on Nov. 20, 2020, now Pat. No. 11,957,365.

(51) Int. Cl.

*A61B 17/22* (2006.01)
*A61B 17/00* (2006.01)

(52) U.S. Cl.

CPC .... *A61B 17/22* (2013.01); *A61B 2017/00199* (2013.01); *A61B 2017/00561* (2013.01); *A61B 2017/22041* (2013.01); *A61B 2017/22079* (2013.01)

(58) Field of Classification Search

CPC .......... A61B 17/22; A61B 2017/00199; A61B 2017/00561; A61B 2017/22041; A61B 2017/22079; A61M 1/7411; A61M 1/7413; A61M 1/7415; A61M 1/743; A61M 1/75; A61M 1/77; A61M 1/772

See application file for complete search history.

(56) References Cited

U.S. PATENT DOCUMENTS 4,941,872 A * 7/1990 Felix .................... A61M 1/774 604/27
5,098,387 A 3/1992 Wiest et al.
5,380,173 A 1/1995 Hellstrom
6,203,296 B1 3/2001 Ray et al.
6,234,992 B1 5/2001 Haight et al.
6,984,239 B1 1/2006 Drasler et al.
7,918,822 B2 4/2011 Kumar et al.
(Continued)

OTHER PUBLICATIONS

Extended Search Report from counterpart European Application No. 21202158.8 dated May 11, 2022, 15 pp.
(Continued)

*Primary Examiner* — Diane D Yabut
*Assistant Examiner* — Christian D Knauss
(74) *Attorney, Agent, or Firm* — Shumaker & Sieffert, P.A.

(57) ABSTRACT

In some examples, a medical aspiration system includes a vacuum source; a vacuum tube coupled to the vacuum source; a vent tube; and a device configured to convert a constant suction force from the vacuum source into a periodic suction force, the device including a housing configured to receive a portion of the vacuum tube and a portion of the vent tube; a first plunger; a second plunger; and a rotatable cam configured to cause the first plunger to periodically compress the vacuum tube and to cause the second plunger to periodically compress the vent tube.

15 Claims, 8 Drawing Sheets

(56) References Cited

U.S. PATENT DOCUMENTS

| | | | | |
|---|---|---|---|---|
| 8,297,954 | B2 | 10/2012 | Moubayed | |
| 8,801,666 | B2 | 8/2014 | Kuebler et al. | |
| 8,882,481 | B2 | 11/2014 | Harr | |
| 8,939,927 | B2 | 1/2015 | Sorenson et al. | |
| 10,531,883 | B1 * | 1/2020 | Deville | A61M 25/0075 |
| 11,957,365 | B2 * | 4/2024 | Skujins | A61M 1/77 |
| 2004/0059284 | A1 | 3/2004 | Nash | |
| 2010/0209263 | A1 | 8/2010 | Mazur | |
| 2012/0041360 | A1 | 2/2012 | Gerg et al. | |
| 2014/0271273 | A1 | 9/2014 | Carpenter | |
| 2017/0296712 | A1 * | 10/2017 | Anton | A61M 5/20 |
| 2018/0296738 | A1 | 10/2018 | King et al. | |
| 2019/0143009 | A1 | 5/2019 | Heaton et al. | |
| 2019/0201598 | A1 | 7/2019 | Ehlert | |
| 2019/0275219 | A1 | 9/2019 | Ehlert et al. | |
| 2019/0381223 | A1 | 12/2019 | Culbert et al. | |
| 2020/0093503 | A1 | 3/2020 | Deville et al. | |

OTHER PUBLICATIONS

Partial Search Report from counterpart European Application No. 21202158.8 dated Feb. 8, 2022, 19 pp.
Prosecution History from U.S. Appl. No. 17/100,360, dated May 25, 2023 through Dec. 20, 2023, 39 pp.
Response to Rule 69 and Rule 70a(1) from counterpart European Application No. 21202158.8 dated Feb. 8, 2022, filed Jun. 14, 2022, 72 pp.

* cited by examiner

ASPIRATION PULSATOR

This application is a continuation of U.S. patent application Ser. No. 17/100,360, which was filed on Nov. 20, 2020, and is entitled, "ASPIRATION PULSATOR," the entire content of which is incorporated herein by reference.

TECHNICAL FIELD

This disclosure relates to medical aspiration.

BACKGROUND

In some cases, medical aspiration can be used to remove material from a patient. For example, medical aspiration can be used to remove an occlusion from a blood vessel of a patient.

SUMMARY

This disclosure describes example devices and systems configured to control a suction force applied to a medical catheter during a medical aspiration procedure, and related methods. In examples described herein, an aspiration pulsator is configured to convert a continuous suction force into a periodic suction force by at least periodically compressing a portion of a vacuum tube that is fluidically coupled to a catheter. In some examples, the aspiration pulsator is configured to provide an alternating suction and venting to a lumen of the catheter by at least periodically compressing a vacuum tube and a vent tube received within an internal volume of a housing of the aspiration pulsator. In some such examples, the alternating suction and venting may more-effectively dislodge a thrombus from a vasculature of a patient, thereby improving medical aspiration procedures.

The devices, systems, and techniques of this disclosure may provide a clinician with more-direct control of cyclic aspiration at the point of connection to a treatment catheter. For example, due to the relatively compact size of the aspiration pulsator, the aspiration pulsator may be sterilizable, enabling the aspiration pulsator to be positioned within a sterile field and relatively close to a clinician during a medical procedure. Additionally, the aspiration pulsators described herein can be battery-powered, which enable the aspiration pulsator to operate without external electrical connections, thereby preserving the sterile field during the medical procedure.

In some examples, a device configured to convert a constant suction force to a periodic suction force includes: a housing configured to receive a portion of a vacuum tube and a portion of a vent tube; a first plunger; a second plunger; and a rotatable cam configured to cause the first plunger to periodically compress the vacuum tube and to cause the second plunger to periodically compress the vent tube.

In some examples, an aspiration system includes a vacuum source; a vacuum tube coupled to the vacuum source; a vent tube; and a device including: a housing configured to receive a portion of the vacuum tube and a portion of the vent tube; a first plunger; a second plunger; a rotatable cam configured to rotate to cause the first plunger to periodically compress the vacuum tube and to cause the second plunger to periodically compress the vent tube; and a motor configured to rotate the rotatable cam; and control circuitry configured to configured to control the motor to control the rotation of the rotatable cam.

In some examples, an aspiration system includes a sterile field; an aspiration tube located in the sterile field; a motorized pulsator located in the sterile field and coupled to the aspiration tube; wherein the pulsator is operable to open and close the aspiration tube to flow of liquid through the tube.

This disclosure also describes examples of methods of using the aspiration systems and devices.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

This disclosure describes devices and systems configured to control a suction force applied to a medical catheter during a medical aspiration procedure, medical aspiration systems (e.g., vascular aspiration systems) including such devices and systems, and corresponding methods. In examples described herein, an aspiration pulsator is configured to convert a continuous suction force into a periodic or time-varying suction force by at least periodically compressing a portion of a vacuum tube that is configured to fluidically couple to a catheter. For example, in some examples, the aspiration pulsator is configured to convert a continuous suction force into a periodic suction force by at least periodically compressing a portion of a vacuum tube that is configured to fluidically couple to a catheter. Compressing a tube (e.g., a vacuum tube or a vent tube) fully or partially closes the tube, and therefore modifies the flow of fluid through the tube. In some examples, the aspiration pulsator is configured to provide an alternating suction and venting to a lumen of the catheter by at least periodically compressing a vacuum tube and periodically compressing a vent tube, both tubes being received and retained within an internal space defined by a housing of the aspiration pulsator. In some such examples, the alternating suction and venting or irrigation may more-effectively dislodge a thrombus from a vasculature of a patient, thereby improving medical aspiration procedures.

The example aspiration pulsators described herein may provide a clinician (e.g., the surgeon) with more direct control of cyclic aspiration at the point of connection to a treatment catheter. For example, due to the relatively compact size of the aspiration pulsator, the aspiration pulsator may be sterilizable without adverse impacts to its structural integrity, enabling the aspiration pulsator to be positioned within a sterile field and relatively close to a clinician during a medical procedure. The clinician can therefore relatively quickly adjust the aspiration pulsators described herein to adjust (e.g., modify or vary) a suction force applied to a catheter, to adjust a frequency of cyclical aspiration, to connect or disconnect the catheter to the aspiration tubing, or the like, thereby enabling the clinician to relatively quickly react and adapt to the dynamic needs of each aspiration procedure. Additionally, the aspiration pulsators described herein can be battery-powered, which enable the aspiration pulsators to operate without external electrical connections, thereby preserving the sterile field during the medical procedure.

Figure 1A:
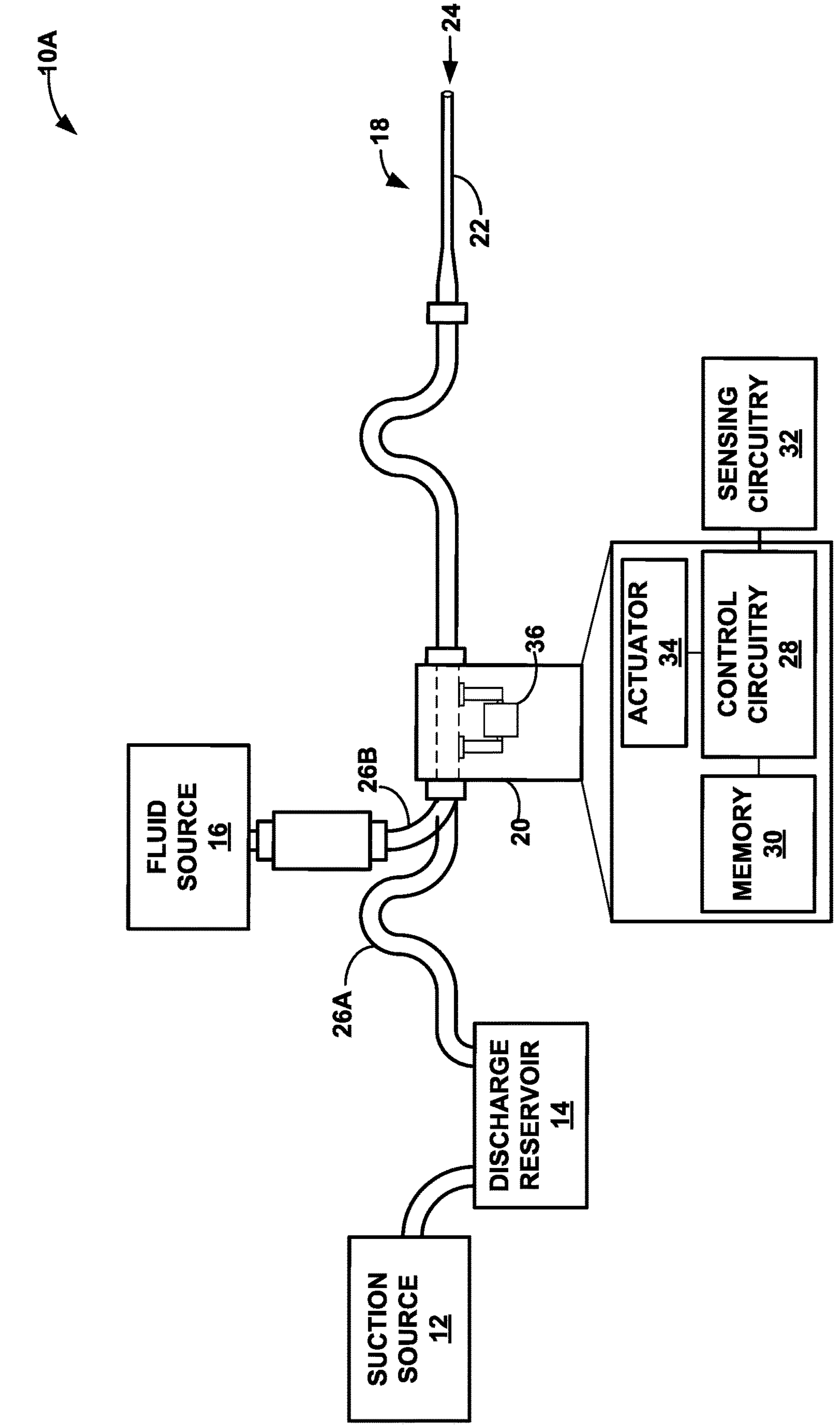
FIG. 1A is a schematic diagram illustrating an example aspiration system including an aspiration pulsator.

FIG. 1A is a schematic diagram illustrating an example medical aspiration system 10A including a suction source 12, a discharge reservoir 14, a fluid source 16, an aspiration catheter 18, and an aspiration pulsator 20. Aspiration system 10A may be used to treat a variety of conditions, including thrombosis. Thrombosis occurs when a thrombus (e.g., a blood clot or other material such as plaques or foreign bodies) forms and obstructs vasculature of a patient. For example, medical aspiration system 10A may be used to treat an ischemic insult, which may occur due to occlusion of a blood vessel (arterial or venous) that deprives brain tissue, heart tissue or other tissues of oxygen-carrying blood.

Aspiration system 10A is configured to remove fluid via catheter 18, e.g., draw fluid from catheter 18 into discharge reservoir 14, via a suction force applied by suction source 12 to catheter 18 (e.g., to an inner lumen of catheter 18). Catheter 18 includes an elongated body 22 defining a lumen (not shown) terminating in a mouth 24. To treat a patient with thrombosis, a clinician may position mouth 24 of catheter 18 in a blood vessel of the patient near the thrombus or other occlusion, and apply a suction force (also referred to herein as suction, vacuum force, or negative pressure) to the catheter 18 (e.g., to one or more lumens of the catheter) to engage the thrombus with suction force at mouth 24 of the catheter. For example, suction source 12 can be configured to create a negative pressure within the inner lumen of catheter 18 to draw a fluid, such as blood, an aspiration fluid, more solid material, or a mixture thereof, into the inner lumen via mouth 24 of catheter 18. The negative pressure within the inner lumen can create a pressure differential between the inner lumen and the environment external to at least a distal portion of catheter 18 that causes fluid and other material to be introduced into the inner lumen via mouth 24. For example, the fluid may flow from patient vasculature, into the inner lumen via mouth 24, and subsequently through aspiration tubing 26A (also referred to herein as "vacuum tube 26A") into discharge reservoir 14.

Once mouth 24 of aspiration catheter 18 has engaged the thrombus, the clinician may remove aspiration catheter 18 with the thrombus held within mouth 24 or attached to the distal tip of elongated body 22, or suction off pieces of the thrombus (or the thrombus as a whole) until the thrombus is removed from the blood vessel of the patient through a lumen of aspiration catheter 18 itself and/or through the lumen of an outer catheter in which aspiration catheter 18 is at least partially positioned. The outer catheter can be, for example, a guide catheter configured to provide additional structural support to the aspiration catheter. The aspiration of the thrombus may be part of an aspiration procedure, such as, but not limited to, a medical procedure using A Direct Aspiration First Pass Technique (ADAPT) for acute stroke thrombectomy, or any other procedure for aspiration of thrombus or other material from the neurovasculature or other blood vessels. In addition, aspiration of thrombus can be performed concurrently with use of a thrombectomy device, such as a stent retriever, to facilitate removal of thrombus via mechanical thrombectomy as well as via aspiration.

In some examples, aspiration system 10A is also configured to deliver fluid from a fluid source 16, for example, a fluid reservoir different from discharge reservoir 14, through aspiration tubing 26B (also referred to herein as "irrigation tube 26B" or "flush tube 26B") and into the inner lumen of catheter 18 via a positive pressure applied by suction source 12.

As used herein, "suction force" is intended to include, within its scope, related concepts such as suction pressure, vacuum force, vacuum pressure, negative pressure, fluid flow rate, and the like. A suction force can be generated by a vacuum, e.g., by creating a partial vacuum within a sealed volume fluidically connected to a catheter, or by direct displacement of liquid in a catheter or tubing via (e.g.) a peristaltic pump, or otherwise. Accordingly, suction forces or suction as specified herein can be measured, estimated, computed, etc. without need for direct sensing or measurement of force. A "higher," "greater," or "larger" (or "lower," "lesser," or "smaller") suction force described herein may refer to the absolute value of the negative pressure generated by the suction source on a catheter or another component, such as a discharge reservoir 14.

In some examples, suction source 12 can comprise a pump (also referred to herein as "pump 12" or "vacuum source 12"). The suction source 12 can include one or more of a positive displacement pump (e.g., a peristaltic pump, a rotary pump, a reciprocating pump, or a linear pump), a direct-displacement pump (e.g., a peristaltic pump, or a lobe, vane, gear, or piston pump, or other suitable pumps of this type), a direct-acting pump (which acts directly on a liquid to be displaced or a tube containing the liquid), an indirect-acting pump (which acts indirectly on the liquid to be displaced), a centrifugal pump, and the like. An indirect-acting pump can comprise a vacuum pump, which displaces a compressible fluid (e.g., a gas such as air) from the evacuation volume (e.g., discharge reservoir 14, which can comprise a canister), generating suction force on the liquid. Accordingly, the evacuation volume (when present) can be considered part of the suction source. In some examples, suction source 12 includes a motor-driven pump, while in other examples, suction source 12 can include a syringe configured to be controlled by control circuitry 28, and mechanical elements such as linear actuators, stepper motors, etc. As further examples, the suction source 12 could comprise a water aspiration venturi or ejector jet.

Control of suction source 12 can comprise control, operation, and the like, of any one or combination of the component(s) making up the suction source. Accordingly, in examples in which suction source 12 includes a pump and an evacuation volume, control of the suction source can comprise control of only the pump, of only the evacuation volume, or of both of those components. As in examples in which suction source 12 includes only a pump, control of suction source 12 comprises control of the pump.

In some examples, suction source 12 is configured for bi-directional operation. For example, suction source 12 may be configured to create a negative pressure that draws fluid from the inner lumen of catheter 18 in a first flow direction and create a positive pressure that pumps fluid to catheter 18 and through inner the lumen in a second, opposite flow direction. As an example of this bi-directional operation, an operator of aspiration system 10A may operate suction source 12 to pump an aspiration/irrigating fluid, such as saline, from an aspiration fluid reservoir 16 via irrigation tube 26B to flush and/or prime catheter 18 (e.g., an infusion state) and subsequently draw fluid from a site of mouth 24 of catheter 18, such as saline and/or blood, via vacuum tube 26A, into discharge reservoir 14.

Aspiration system 10A includes control circuitry 28 configured to control a suction force applied by suction source 12 to catheter 18. For example, control circuitry 28 can be configured to directly control an operation of suction source 12 to vary the suction force applied by suction source 12 to the inner lumen of catheter 18, e.g. by controlling the motor speed, or stroke length, volume or frequency, or other operating parameters, of suction source 12. As another example, control circuitry 28 can be configured to control an aspiration pulsator 20, which is configured to convert a continuous suction force from suction source 12 into a periodic or time-varying suction force. Other techniques for modifying a suction force applied by suction source 12 to the inner lumen of catheter 18 can be used in other examples.

Control circuitry 28, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 28 may include multiple components, such as any combination of one or more microprocessors, one or more DSPs, one or more ASICs, or one or more FPGAs, as well as other discrete or integrated logic circuitry, and/or analog circuitry. In some examples, control circuitry 28 may further include, additionally or alternatively to electric-based processors, one or more controls that operate using fluid motion power (e.g., hydraulic power) in combination with or in addition to electricity. For example, control circuitry 28 can include a fluid circuit comprising a fluid circuit comprising a plurality of fluid passages and switches arranged and configured such that, when a fluid (e.g., liquid or gas) flows through the passages and interacts with the switches, the fluid circuit performs the functionality of control circuitry 28 described herein.

Memory 30 may store program instructions, such as software, which may include one or more program modules, which are executable by control circuitry 28. When executed by control circuitry 28, such program instructions may cause control circuitry 28 to provide the functionality ascribed to control circuitry 28 herein. The program instructions may be embodied in software and/or firmware. Memory 30, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Although control circuitry 28 and memory 30 are shown in FIG. 1A as being part of pulsator 20, in other examples, control circuitry 28 and/or memory 30 can be part of a device that is physically separate from pulsator 20.

Pulsator 20 is configured to convert a continuous suction force from suction source 12 into a periodic or time-varying suction force by at least periodically compressing vacuum tube 26A closed (or partially closed) to inhibit or disrupt a flow of fluids through the tube 26A. Aspiration pulsator 20 can include flow restrictor 36 configured for selective actuation as needed to fluidically couple or uncouple catheter 18 to or from suction source 12 in accordance with control of aspiration system 10A. Pulsator 20 can be employed to switch on, switch off, vary (e.g., oscillate, pulse, etc.), and the like, the application of suction force from suction source 12 to catheter 18. Accordingly, pulsator 20 can fluidically couple or uncouple catheter 18 to or from suction source 12 as needed. For example, flow restrictor 36 of pulsator 20 can include a tubing compressor configured to open and close the connection of catheter 18 to discharge reservoir 14 (e.g., when no fluid source 16 is present) or alternatingly switch the connection of catheter 18 to discharge reservoir 14 and to fluid source 16.

In the example shown in FIG. 1A, control circuitry 28 is configured to control an amount of suction force applied by suction source 12 to the inner lumen of catheter 18 by at least controlling pulsator 20. In some examples, suction source 12 is configured to apply a substantially continuous suction force (e.g., continuous or nearly continuous to the extent permitted by the hardware) to discharge reservoir 14, and the amount of this suction force that is transferred to the inner lumen of catheter 18 may be adjusted by pulsator 20. For example, in some examples, pulsator 20 is configured to connect to one or both of vacuum tube 26A and irrigation tube 26B, in a manner that enables pulsator 20 to selectively open or close (in either case, completely or partially) vacuum tube 26A and/or irrigation tube 26B. Accordingly, pulsator 20 can be configured to receive and retain a portion of vacuum tube 26A and/or irrigation tube 26B within a receptacle or interior space defined by an external housing of pulsator 20. Pulsator 20 includes a flow restrictor 36 configured to periodically compress the retained portions of vacuum tube 26A and irrigation tube 26B (collectively, "tubes 26"). This compression of tubes 26 reduces the size of the cross-sectional area of the internal volume or lumen of the tubes, thereby periodically inhibiting, interrupting, or otherwise modifying the flow of a fluid or fluids (e.g., liquids and/or gases) through tubes 26.

In some examples, suction source 12 is configured to apply pulsed aspiration, e.g., by alternating within a repeating cycle between "on" and "off" phases (during the latter of which no suction force, or reduced suction force is applied to vacuum tubing 26A), rather than applying a substantially continuous suction force. The pulsed aspiration can be used alone or in combination with pulsator 20 to vary the amount of suction force applied to the inner lumen of catheter 18, e.g., to aspirate a clot from vasculature of a patient.

In some examples, flow restrictor 36 of pulsator 20 comprises one or more actuators (e.g., the illustrated plungers 48A, 48B (collectively, "plungers 48" of FIG. 2)) configured to compress a respective tube 26A, 26B from a default "open" configuration to a closed or flow-restricted configuration. For example, control circuitry 28 may be configured to control plungers 48 to open and close tubing 26A and tubing 26B at particular times in accordance with the example control techniques disclosed herein. In a first position of flow restrictor 36 (e.g., first positions of plungers 48), vacuum tube 26A is open and irrigation tube 26B is closed, and in a second position of flow restrictor 36 (e.g., second positions of plungers 48), vacuum tube 26A is closed and irrigation tube 26B is open.

Although plungers 48A, 48B are illustrated and discussed in and with respect to FIGS. 2A-5, the actuator(s) employed in pulsator 20/40/70/80/90 to open and close vacuum tube 26A and/or irrigation tube 26B can take a variety of alternative forms, such as rotating cam(s) with lobe(s) or surfaces (s) that impinge on tube(s) 26A, 26B at one or more positions within a revolution of the cam(s) employed in pulsator 20; linear or rotary actuator(s) which can be electrically, electromagnetically, pneumatically or hydraulically driven to open and close vacuum tube 26A and/or irrigation tube 26B. Such linear or rotary actuator(s) can be linear solenoid(s), rotary solenoid(s), or piezoelectric driven linear or rotary actuator(s).

It is believed that cyclically controlling the opening and compressing of vacuum tube 26A and/or vent tube 26C via aspiration pulsator 20 may more quickly and/or more effectively remove a thrombus from a blood vessel of a patient by varying an amount of suction force applied to the thrombus over time.

Figure 1B:
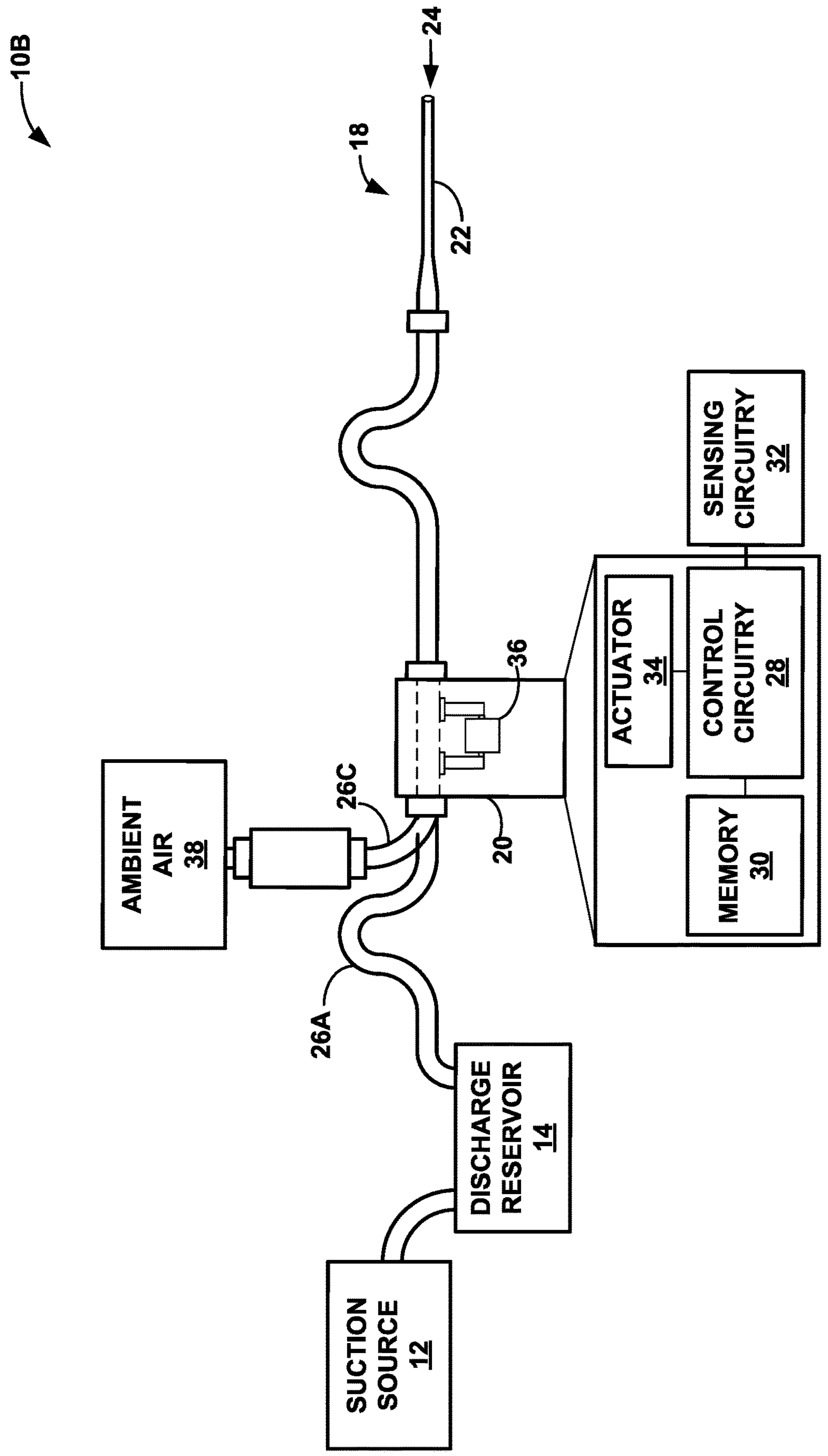
FIG. 1B is a schematic diagram illustrating another example aspiration system including an aspiration pulsator.

FIG. 1B is a schematic diagram illustrating another example aspiration system 10B, which is similar to aspiration system 10A of FIG. 1A, but does not include fluid source 16. As shown in FIG. 1B, in some cases, aspiration system 10B is configured to vent the inner lumen of catheter 18 to ambient air 38 via vent tube 26C. Thus, instead of being fluidically coupled to fluid source reservoir 16, vent tubing 26C can terminate in an opening to ambient air. For the purposes of describing the functionality of aspiration pulsator 20, irrigation tubing 26B of FIG. 1A and vent tubing 26C of FIG. 1B may be used interchangeably throughout this disclosure.

As detailed further below with respect to FIG. 6, in some examples, control circuitry 28 is configured to control pulsator 20 to periodically compress vacuum tube 26A to modify a suction force applied by suction source 12 to the inner lumen of catheter 18 based on a particular timing, which can be referred to as "suction frequency." The suction frequency can be a fixed frequency over a period of time or can vary over the period of time. For example, aspiration pulsator 20 may be controlled based on a cardiac cycle of a patient, which may be determined, detected, or sensed via one or more signals from the patient. For example, in some examples, aspiration system 10A includes sensing circuitry 32, which is configured to generate signals (also referred to herein physiological signals) indicative of physiological parameters and communicate the physiological signals to control circuitry 28. Sensing circuitry 32 may include any sensing hardware configured to sense a physiological parameter of a patient, such as, but not limited to, one or more electrodes, optical receivers, pressure sensors, blood pressure cuffs, or the like. In some examples, the sensed physiological signals may include signals indicative of a cardiac cycle of a patient, such as, but not limited to, an electrocardiogram (ECG), an electrogram (EGM), a photoplethysmogram (PPG), or a blood pressure signal. Thus, in some examples, sensing circuitry 32 can be configured to include any suitable hardware configured to sense an electrical cardiac signal, blood pressure, or blood oxygen saturation (e.g., pulse oximetry) of a patient. In some examples, control circuitry 28 is configured to receive one or more signals generated by sensing circuitry 32 and indicative of a cardiac cycle of a patient, and control suction source 12 and/or pulsator 20 based on the signals.

Figure 2A:
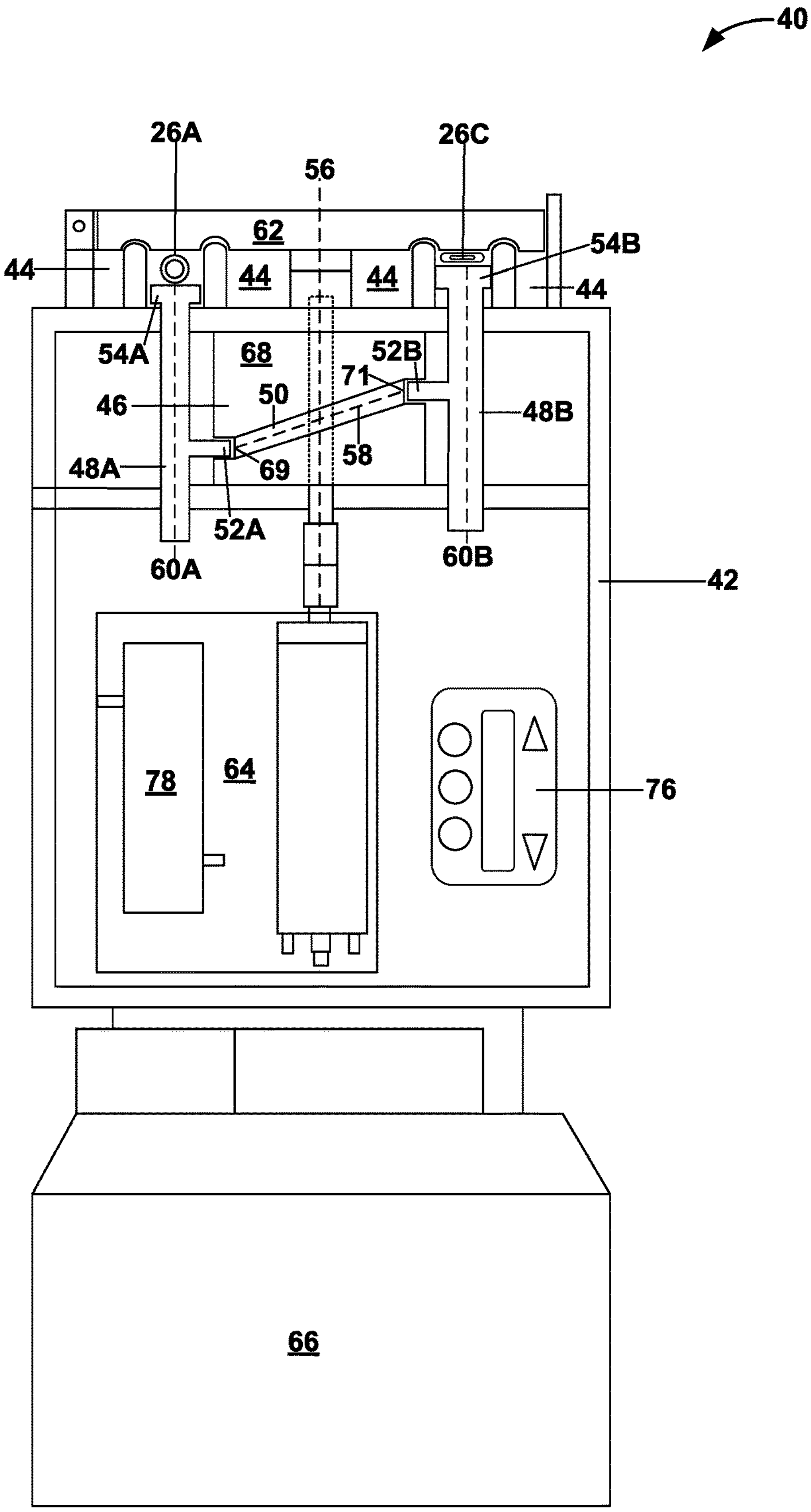
FIG. 2A is a cross-sectional view of an example of the aspiration pulsator of FIGS. 1A and 1B.

FIG. 2A is a schematic cross-sectional view of an example aspiration pulsator 40, which is an example of aspiration pulsator 20 of FIG. 1A. Pulsator 40 is configured to convert a constant or continuous suction force (e.g., from suction source 12 of FIG. 1A) into a varying or periodic suction force. Pulsator 40 includes an external housing 42 having a door 62 and defining an interior space 44 configured to receive a portion of vacuum tube 26A and, optionally, a portion of vent tube 26C. Pulsator 40 further includes a rotatable cam 46 defining a circumferential groove 50, a first actuator (e.g., plunger 48A) and a second actuator (e.g., plunger 48B) (collectively, "plungers 48"), a motor 64, and a removable battery 66.

Rotatable cam 46 is configured to rotate about a central longitudinal axis 56 to cause the first plunger 48A to periodically compress the vacuum tube 26A, and configured to cause the second plunger 48B to periodically compress the vent tube 26C. In the example shown in FIGS. 2A and 2B, rotatable cam 46 includes a cylindrical body 68 defining a circumferential groove 50 configured to receive an arm 52A of the first plunger 48A (or a structure mechanically coupled to the first plunger 48A) and an arm 52B of the second plunger 48B (or a structure mechanically coupled to the second plunger 48B). Rotation of the cylindrical body 68 of cam 46 causes a second portion 54A of first plunger 48A to periodically compress vacuum tube 26A, and causes a second portion 54B of second plunger 48B to periodically compress vent tube 26C. For example, the open or closed (e.g., compressed) configuration of tubes 26 depends on the relative locations of arms 52 of plungers 48 within groove 50. In some examples, both vacuum tube 26A and vent tube 26C may simultaneously be at least partially compressed, e.g., when neither of arms 52 of plungers 48 is located within a proximal-most portion 69 (FIG. 2B) of groove 50. In FIG. 2A, plunger 48B is compressing vent tube 26C, which is shown in a closed configuration, and vacuum tube 26A is uncompressed and in an open configuration. At other times, however, plunger 48A may be compressing vacuum tube 26A and/or vent tube 26C may be uncompressed.

In some examples, vacuum tube 26A and vent tube 26C are fluidically coupled to the inner lumen of an aspiration catheter 18 (FIG. 1A). In such examples, a speed of rotation of rotatable cam 46 establishes the frequency of the periodic suction force within the lumen of the aspiration catheter 18 via the vacuum tube 26A and the vent tube 26C.

Figure 2B:
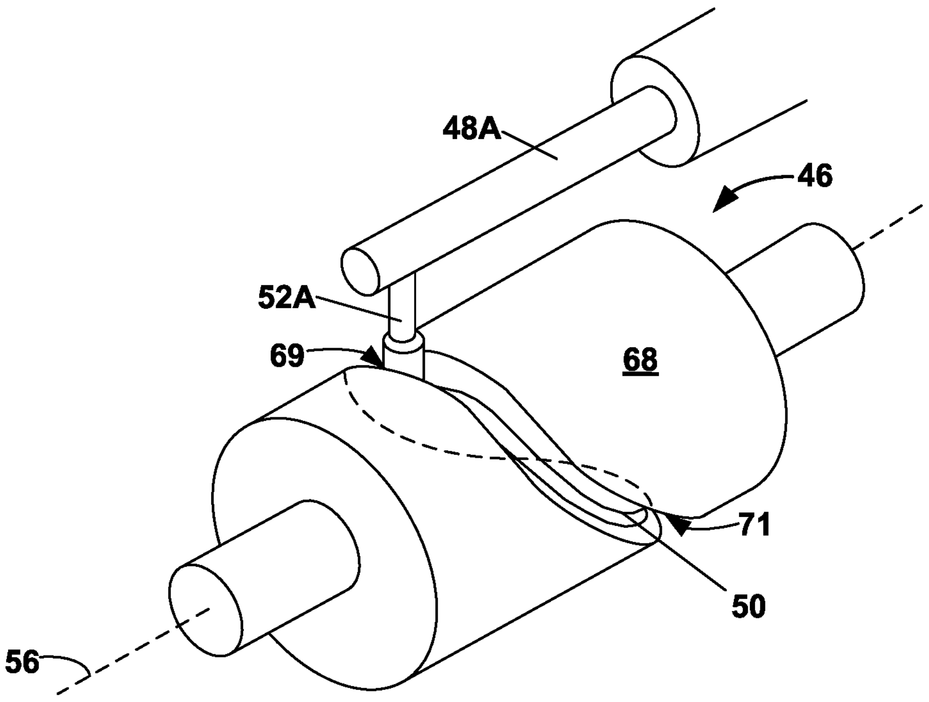
FIG. 2B is a perspective view of an example of the rotatable cam of the aspiration pulsator of FIG. 2A.

In the example of FIGS. 2A and 2B, circumferential groove 50 of rotatable cam 46 includes a substantially helical-shaped groove that extends both longitudinally (e.g., axially) and circumferentially with respect to a longitudinal axis 56 of the cylindrical body of rotatable cam 46. When viewed from the side perspective shown in FIG. 2A, helical groove 50 substantially conforms to a linear groove axis 58. Linear groove axis 58 extends from a proximal-most groove portion 69 to a distal-most groove portion 71, wherein groove axis 58 is oriented at an angle with respect to central longitudinal axis 56 of rotatable cam 46.

Due to the helical shape of groove 50, as rotatable cam 46 rotates about central longitudinal axis 56, surfaces of rotatable cam 46 defining circumferential groove 50 contact arms 52 of plungers 48, applying alternating proximal and distal forces to arms 52, thereby causing plungers 48 to move proximally and distally within groove 50 of cylindrical body 68 (e.g., along directions parallel to central longitudinal axis 56), and causing distal ends 54 of plungers 48 to move closer to and farther away from tubes 26.

In some examples, plungers 48 are generally linear in shape, e.g., substantially elongated and extending along a respective linear plunger axis 60A, 60B (collectively, "plunger axes 60"). In some such examples, rotatable cam 46 is configured to rotate to cause the first plunger 48A to periodically compress the vacuum tube 26A in a distal direction, e.g., in a direction away from the cylindrical body of rotatable cam 46. Similarly, rotatable cam 46 is configured to rotate to cause the second plunger 48B to periodically compress the vent tube 26C in a distal direction, e.g., in a direction away from the cylindrical body of rotatable cam 46.

Figure 5:
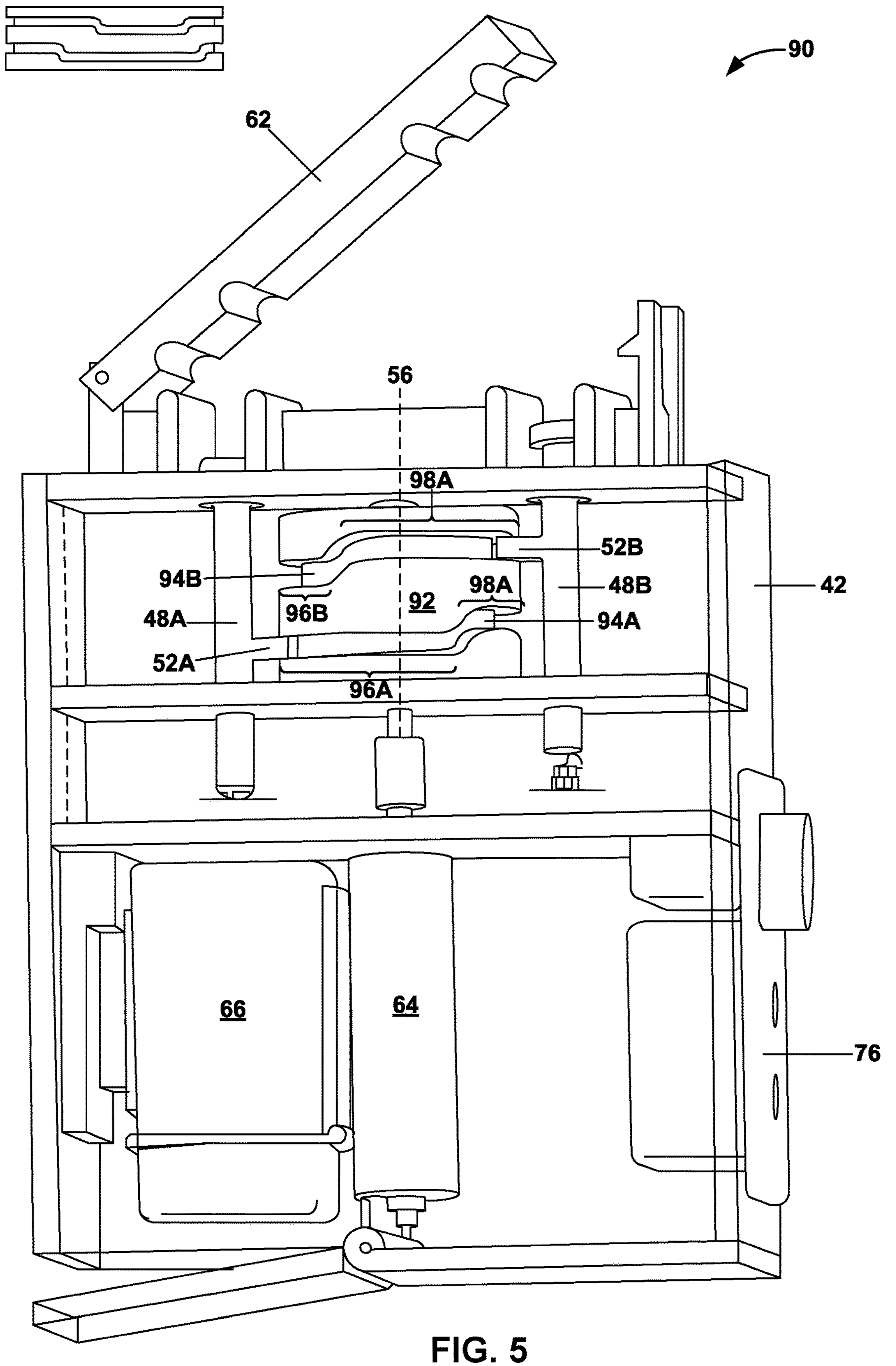
FIG. 5 is a perspective view of another example of the aspiration pulsator of FIGS. 1A and 1B.

Door 62 is configured to open to receive and retain vacuum tube 26A and, optionally, vent tube 26C within interior space 44, which may be at least partially defined by an interior surface of door 62. For example, as shown in FIG. 5, door 62 may be pivotably connected to the rest of housing 42 via a hinge. In other examples, door 62 may be fully removable from the rest of housing 42.

In some examples, first plunger 48A and second plunger 48B are configured to distally compress tubes 26A, 26C, respectively, between a distal-most surface of distal portions 54 of each plunger 48, and an interior surface of door 62. In other examples, vacuum tube 26A and vent tube 26C may integrally formed with (e.g., mechanically coupled to) aspiration pulsator 40. In some examples, door 62 includes a quick-release door having a latch or other similar mechanism configured to allow a user to easily close, secure, and re-open door 62 in order to retain and release tubes 26 as needed.

Pulsator 40 includes a motor 64 configured to cause rotatable cam 46 to rotate about central longitudinal axis 56. Motor 64 may include, for example, a direct current (DC) motor and gearbox, such as a Portescap™ mini motor available from the Danaher Corporation of Washington, D.C. Motor 64, as well as other components of pulsator 40, can be configured to be sterilizable, e.g., sterilized via heat and/or gas, without adverse impacts to the functionality of motor 64.

Figure 3:
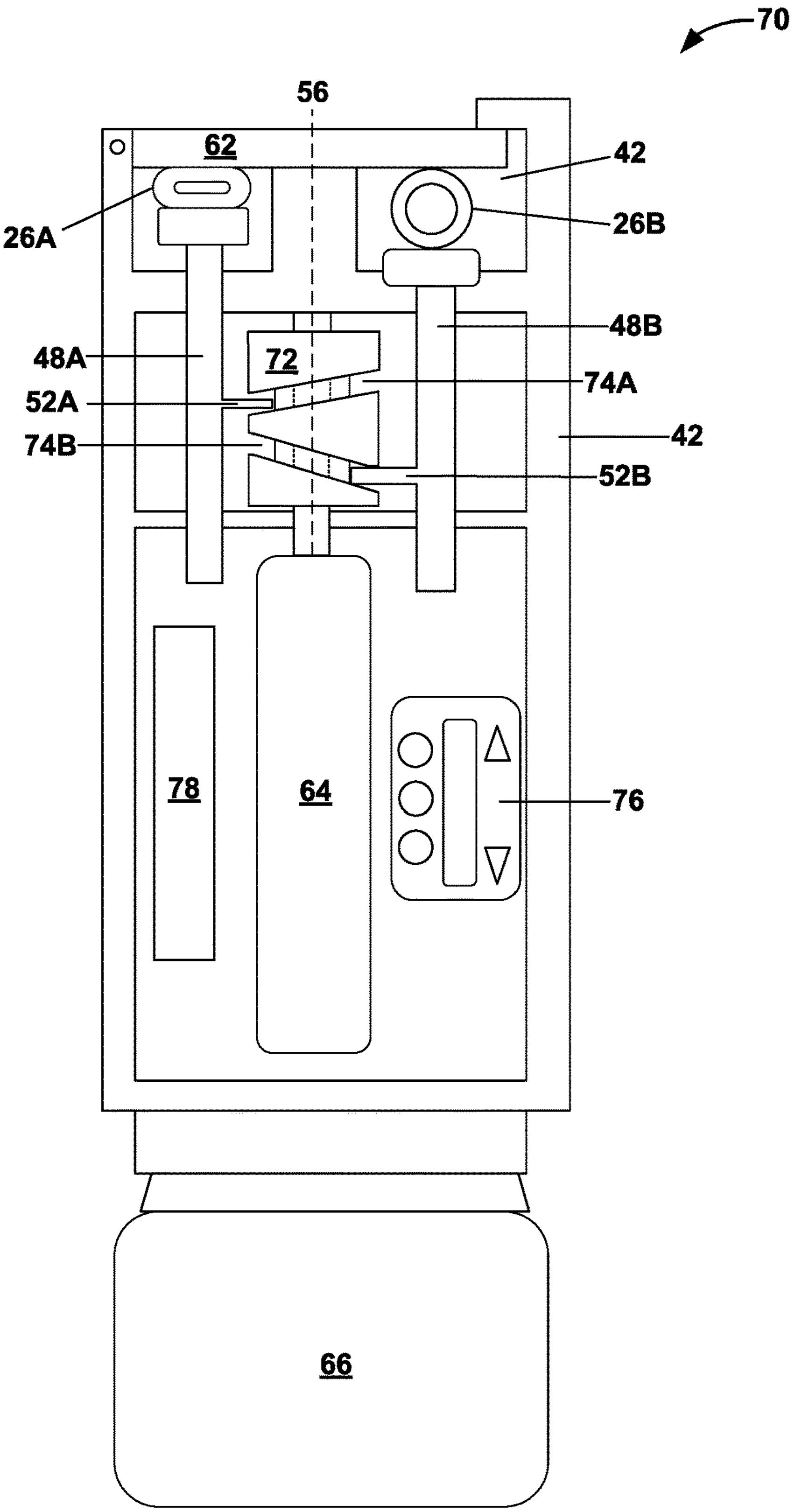
FIG. 3 is a cross-sectional view of another example of the aspiration pulsator of FIGS. 1A and 1B.

In some examples, but not all examples, pulsator 40 includes a removable battery 66 configured to provide electrical power to motor 64. As shown in FIGS. 2A and 3, in some examples, removable battery 66 is configured to attach to an exterior surface of the housing 42 of pulsator 40. In other examples, such as the examples shown in FIGS. 4 and 5, removable battery 66 may be retained within housing 42. In either example, battery 66 is configured to be easily removable from housing 42 to facilitate sterilizability of pulsator 40, and in some cases, of battery 66 as well. In other examples, battery 66 may be disposable and replaceable. In some examples, battery 66 includes a Desoutter™ battery pack, available from Desoutter Tools of Saint-Herblain, Loire-Atlantique, France. In other examples, battery 66 includes a Tadiran™ TLM sterilizable battery pack, available from Saft Groupe S.A. of Levallois-perret, France. In any of the embodiments of pulsator 20/40/70/80/90 disclosed herein, a battery (such as battery 66) may be employed as a power source; alternatively or in addition, a wired connection to "wall power" or "mains power" may be employed instead. Additionally or alternatively, pulsator 40 may be powered by hydraulic power or fluid-motion power.

As shown in FIG. 2A, in some examples, pulsator 40 includes a user-interface (UI) control panel 76. Control panel 76 may be operatively coupled to control circuitry 78, which may include any or all of control circuitry 28 of FIG. 1A, actuator 34 of FIG. 1A, and/or the motor controller of motor 64. Control circuitry 78 is configured to at least control a speed of rotation of rotatable cam 46. For example, control circuitry 78, in response to user input received via control panel 76, may be configured to start and stop (e.g., pause) a rotation of rotatable cam 46, or otherwise operate (e.g., start, stop, pause, advance, retract, rotate in one direction, rotate in the opposing direction, and/or displace to or toward an endpoint in a linear or angular fashion) the actuator(s) employed to open and/or close vacuum tube 26A and/or irrigation tube 26B, as is the case with all of the embodiments of the pulsator disclosed herein. In some examples, control circuitry 78 is configured to enable a user, via control panel 76, to select a frequency of rotation of cam 46, corresponding to a frequency of compression of vacuum tube 26A (e.g., a suction frequency). For example, control circuitry 78 may enable a user to select a frequency of rotation from a predetermined set of discrete frequencies, to select a frequency within a predetermined range of frequencies, or the like. In some examples, control circuitry 78 is configured to enable a user to select a frequency of rotation of cam 46 of about 1.5 Hz to about 15 Hz, such as about 6 Hz to about 12 Hz (or otherwise control operation of the actuator(s) employed in pulsator 40 to generate an actuation frequency within similar ranges).

Since plungers 48 can each be configured to complete one full proximal-to-distal oscillation for each rotation of rotatable cam 46, a higher frequency of rotation of cylindrical body 68 of cam 46 corresponds to a higher pulsed-aspiration frequency of the suction force within the inner lumen of catheter 18 (FIG. 1). In some examples (not shown), rather than groove 50 having a helical shape that defines only a single proximal-most portion 69 and a single distal-most portion 71, in other examples, groove 50 may define a sinusoidal shape that includes a plurality of proximal-most portions and distal-most portions as the groove wraps circumferentially around cylindrical body 68 of cam 46. In some such examples, the pulsed aspiration frequency of the suction force (e.g., the suction frequency) is a multiple of the frequency of rotation of cam 46, wherein the multiple is equal to the number of proximal-and-distal-portion pairs defined by groove 50. For example, in examples in which groove 50 defines two proximal-distal-portion pairs, the pulsed-aspiration suction frequency would be equal to two times the frequency of rotation of rotatable cam 46. In such examples, from a side view similar to the perspective shown in FIG. 2A, the groove would not conform to a linear groove axis 58, but would instead substantially define a V-shape or U-shape.

In some examples, control circuitry 78 is configured to control a rotational position of rotatable cam 46. For example, UI control panel 76 may include a user input mechanism enabling a user to both pause a rotation of rotatable cam 46, and also to select a particular configuration for vacuum tube 26A or vent tube 26C to either remain open or remain compressed closed while the rotation of rotatable cam 46 is paused. For example, control circuitry 78 may enable a user to relatively quickly adjust aspiration pulsator 40 to periodically compress vacuum tube 26A to adjust a suction force applied to catheter 18 (FIG. 1A), to adjust a frequency of cyclical aspiration, or the like, thereby enabling the clinician to relatively quickly react and adapt to the dynamic needs of each aspiration procedure.

In some examples, control circuitry 78 receives user input from control panel 76, selects a corresponding rotational position of rotatable cam 46, and controls motor 64 to achieve the selected rotational position of rotatable cam 46. In some examples, motor 64 may include a built-in encoder configured to enable control circuitry 78 to precisely control a rotational position of rotatable cam 46 via motor 64. In other examples, aspiration pulsator 40 may include a position sensor configured to determine (e.g., monitor) a rotational position of motor 64 and/or rotatable cam 46 in order to enable control circuitry 78 to control the rotational position of rotatable cam 46 via motor 64. During use, control circuitry 78 receives user input indicative of a desired position in which to pause the rotation of the rotatable cam (e.g., indicative of which of tubes 26 to remain open or closed), and in response, control circuitry 78 is configured to select a time, based on the intended rotational position of rotatable cam 46, at which to pause the rotation of the rotatable cam 46 such that the vacuum tube 26A or the vent tube 26C remains compressed or uncompressed while the rotation of the rotatable cam 46 is paused.

FIG. 3 is a cross-sectional view of another example aspiration pulsator 70, which may be an example of pulsator 20 of FIGS. 1A and 1B. As shown in FIG. 3, pulsator 70 includes a rotatable cam 72, which is similar to rotatable cam 46 of FIG. 2 but unlike rotatable cam 46, rotatable cam 72 includes two separate helical grooves 74A and 74B (collectively, "grooves 74"). First helical groove 74A is configured to receive arm 52A of first plunger 48A and second helical groove 74B is configured to receive arm 52B of second plunger 48B. Coupling plungers 48 to two distinct grooves 74 enables each of plungers 48 to oscillate according to a different relative frequency from one another.

For example, as described above, although not depicted in FIG. 3, either of first groove 74A or second groove 74B may include a different number of proximal-and-distal-most-portion pairs as compared to the other groove. In such examples, each groove would be configured to cause the respective plunger 48 to oscillate at a different frequency than the other plunger. As one non-limiting, illustrative example, first groove 74A having a helical shape defining a single proximal-distal-portion pair would cause plunger 48A to oscillate at a frequency of 5 Hz while rotatable cam 72 rotates at a frequency of 5 Hz, whereas second groove 74B having a sinusoidal shape defining two proximal-distal-portion pairs would cause plunger 48B to oscillate at a frequency of 10 Hz while rotatable cam 72 rotates at a frequency of 5 Hz. Other example shapes of grooves 74 may be contemplated to enable different relative frequencies of oscillation of plungers 48.

Figure 4:
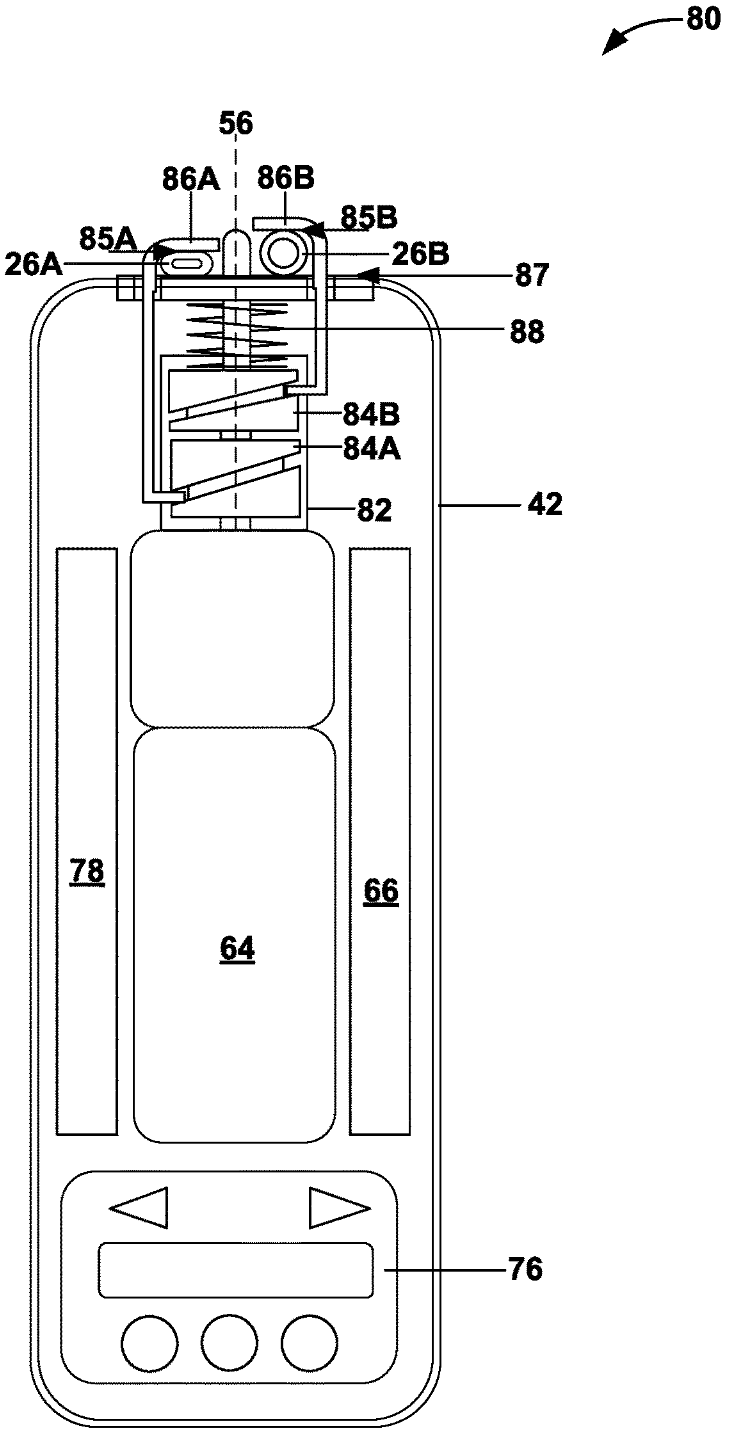
FIG. 4 is a cross-sectional view of another example of the aspiration pulsator of FIGS. 1A and 1B.

FIG. 4 is a cross-sectional view of another example aspiration pulsator 80, which may be an example of aspiration pulsator 20 of FIGS. 1A and 1B. Aspiration pulsator 80 includes a rotatable cam 82, two hook-shaped plungers 86A, 86B (collectively, "plungers 86"), and a clamping spring 88.

Unlike aspiration pulsators 40 and 70, which include rotatable cams 46 and 72 each having a single cylindrical body, aspiration pulsator 80 includes rotatable cam 82 having two distinct cylindrical bodies 84A and 84B. First cylindrical body 84A defines a circumferential groove configured to receive an arm of first plunger 86A. First plunger 86A is configured to compress vacuum tube 26A closed to disrupt a flow of fluid through the tube 26A as first cylindrical body 84A rotates. Similarly, second cylindrical body 84B defines a circumferential groove configured to receive an arm of a second plunger 86B. Second plunger 86B is configured to compress vent tube 26C closed to disrupt a flow of fluid through the tube 26B as second cylindrical body 84B rotates.

First cylindrical body 84A and second cylindrical body 84B may be independently rotatable with respect to one another, enabling control circuitry 78 to independently control a closed or open configuration of vacuum tube 26A and a closed or open configuration of vent tube 26C. For example, by rotating first cylindrical body 84A relative to the second cylindrical body 84B, control circuitry 78 may control the relative points in time at which vacuum tube 26A and vent tube 26C are each in an open configuration or a closed configuration.

In some examples, a user of aspiration pulsator 80 may be able to customize, via control panel 76 and control circuitry 78, a rotational position of first cylindrical body 84A relative to second cylindrical body 84B such that both tubes 26 are compressed closed at the exact same time while cam 82 rotates. In other examples, a user of aspiration pulsator 80 may be able to customize, via control panel 76 and control circuitry 78, a rotational position of first cylindrical body 84A relative to second cylindrical body 84B, such that vacuum tube 26A is compressed closed at the exact same time that vent tube 26C is fully open while cam 82 rotates. In other examples, the user may define or select a periodic offset for the oscillations of plungers 86, via control panel 76 and control circuitry 78, by controlling the rotational orientations of cylindrical bodies 84 with respect to one another.

In some examples, aspiration pulsator 80 of FIG. 4 includes hook-shaped plungers 86. For example, aspiration pulsator 80 is configured to retain tubing 26 between a proximal-facing surface of plungers 86 and an exterior surface of housing 42. Accordingly, plungers 86 are configured to proximally compress tubing 26 (e.g., in a direction toward rotatable cam 82) between proximal-facing surfaces 85A, 85B ("proximal-facing surfaces 85") of plungers 86 and an exterior surface 87 of housing 42 as cylindrical bodies 84 of rotatable cam 82 rotate. In other examples, each of cylindrical bodies 84 may be mechanically coupled to a more-linear shaped plunger like those shown in FIGS. 2A and 3, configured to distally compress tubing 26 (e.g., in a direction away from rotatable cam 82) between a distal-facing surface of plungers and an interior surface of housing 42.

In some examples, aspiration pulsator 80 includes a clamping spring 88 disposed between the rotatable cam 82 and an interior surface of the housing 42. Clamping spring 88 is configured to apply a proximal force to rotatable cam 82 in order to proximally bias the first plunger 86A toward vacuum tube 26A, and to proximally bias the second plunger 86B toward vent tube 26C.

FIG. 5 is a perspective view of another example aspiration pulsator 90, which may be an example of aspiration pulsators 20, 40, 70, and 80. Similar to aspiration pulsator 70 of FIG. 3, aspiration pulsator 90 of FIG. 5 includes a rotatable cam 92 defining two circumferential grooves 94A, 94B (collectively, "grooves 94"). However, unlike the circumferential grooves shown in FIGS. 2A-4, which continuously vary in axial (e.g., proximal-to-distal) position as they advance around the circumference of the rotatable cam, each circumferential groove 94 of FIG. 5 includes a shape defining a first non-zero circumferential arc length comprising a more-proximal groove portion 96A, 96B (collectively, "proximal groove portions 96") and a second non-zero circumferential arc length comprising a more-distal groove portion 98A, 98B (collectively, "distal groove portions 98"). In some examples, each of proximal groove portions 96 and distal groove portions 98 are substantially linear and are oriented substantially perpendicular to central longitudinal axis 56.

Unlike the helical and/or sinusoidal-shaped circumferential grooves shown in FIGS. 2A-4, which enable a virtually continuous proximal-to-distal oscillation motion of plungers 48 and 86, the uneven or disjointed circumferential grooves 94 (e.g., defining at least two distinct circumferential arc lengths 96, 98) separated by an intermediate transitional portion) of rotatable cam 92 of FIG. 5 enable a discontinuous, binary oscillation motion of plungers 48. For example, as rotatable cam 92 rotates about central longitudinal axis 56, arms 52 of plungers 48 may remain located within more-proximal regions 96 of grooves 94 for a first non-zero duration of time, during which time, the respective retained plunger 48 remains in a more-proximal orientation, away from a respective tube 26 (FIGS. 1A-4), and accordingly, the respective tube 26 remains in an open configuration. As grooves 94 of rotatable cam 92 continue to rotate, arms 52 of plungers 48 are eventually received into the more-distal regions 98 of circumferential grooves 94 for a second non-zero duration of time, during which time, the respective plunger 48 remains in a more-distal configuration, thereby compressing the respective tube 26 into a closed configuration against the interior surface of quick-release door 62 of housing 42, thereby disrupting the flow of fluid through the tube. Similarly, as grooves 94 of rotatable cam 92 continue to rotate, proximal extensions 52 of plungers 48 eventually proximally return back to the proximal regions 96 of circumferential grooves 94, thereby allowing tubes 26 to revert back into their respected open configurations.

In some examples, proximal groove regions 96 of circumferential grooves 94 may define different arc lengths than distal groove regions 98. That is, proximal groove regions 96 may occupy either a larger or smaller proportion of the circumference of grooves 94, as compared to the proportion of the circumference of grooves 94 occupied by distal groove regions 98. Different relative proportions of proximal groove regions 96 and distal groove regions 98 correspond to different proportions of the first duration of time that each respective tube 26 remains open, relative to the second duration of time that the tube 26 is compressed closed by the respective plunger 48.

Additionally or alternatively, in some examples, proximal groove region 96A of first circumferential groove 94A may define a different arc length than proximal groove region 96B of second circumferential groove 94B. That is, proximal groove region 96A of groove 94A may occupy either a larger or smaller proportion of the circumference of groove 94A, as compared to the proportion of the circumference of groove 94B occupied by proximal groove region 96B. Different relative proportions of proximal groove region 96A to proximal groove region 96B correspond to different proportions of the second duration of time that vacuum tube 26A is compressed closed by plunger 48A, relative to the second duration of time that vent tube 26C is compressed closed by plunger 48B.

Additionally or alternatively, in some examples, first circumferential groove 94A may be rotationally oriented relative to second circumferential groove 94B so as to define an "overlap" duration of time during which both tubes are either simultaneously open in their respective open configurations, or both simultaneously compressed in their closed configurations. That is, proximal groove region 96A of groove 94A may at least partially circumferentially overlap with proximal groove region 96B of groove 94B such that both vacuum tube 26A and vent tube 26C remain simultaneously open for a predetermined proportion of each complete rotation of rotatable cam 92. In some examples, these overlap durations may be useful for preventing a sharp "jerk" that might otherwise occur from sharp transitions between application of the suction force from vacuum tube 26A and the venting or fluid from vent tube 26C.

A combination of different relative proportions of relative arc lengths of grooves 94 and relative rotational orientations of distal groove region 98A to distal groove region 98B translate to different proportions of the durations of time that vacuum tube 26A is compressed closed by plunger 48A relative to the duration of time that vent tube 26C is compressed closed by plunger 48B. Although not shown in FIG. 5, in some examples, rotatable cam 92 includes two distinct cylindrical bodies (e.g., cylindrical bodies 84 of rotatable cam 82 of FIG. 4) that are rotatable relative to one another, thereby enabling a user to control (e.g., customize) the relative overlap durations of suction via vacuum tube 26A and venting via vent tube 26C.

As one non-limiting, illustrative example, rotatable cam 92 may include a first groove 94A having a distal groove region 98A that occupies about 70% of the circumference of rotatable cam 92, such that vacuum tube 26A is compressed closed for 70% of the duration of each rotation of rotatable cam 92. Similarly, rotatable cam 92 may include a second groove 94B having a distal groove region 98B that occupies about 40% of the circumference of rotatable cam 92, such that vent tube 26C is compressed closed for 40% of the duration of each rotation of rotatable cam 92. Further, first distal groove region 98A may be rotationally oriented relative to second distal groove region 98B so as to define a 5% "overlap" region on either end of both compression cycles. That is, a single rotation of rotatable cam 92 corresponds to a 60% rotational duration during which only vacuum tube 26A is compressed closed, followed by a 5% overlap duration during which both vacuum tube 26A and vent tube 26C are compressed closed, followed by a 30% duration during which only vent tube 26C is compressed closed, followed by another 5% overlap duration during which both vacuum tube 26A and vent tube 26C are compressed closed.

In some examples, pulsator 90 may provide a clinician (e.g., the surgeon) with more direct control of cyclic aspiration at the point of connection to a treatment catheter 18 (FIG. 1). For example, due to the relatively compact size of aspiration pulsator 90, the aspiration pulsator 90 may be sterilizable without adverse impacts to its structural integrity, enabling aspiration pulsator 90 to be positioned within a sterile field and relatively close to a clinician during a medical procedure. The clinician can therefore relatively quickly adjust aspiration pulsator 90 described herein to periodically compress vacuum tube 26A to adjust a suction force applied to catheter 18, to adjust a frequency of cyclical aspiration, to connect or disconnect catheter 18 to aspiration tubing 26, or the like, thereby enabling the clinician to relatively quickly react and adapt to the dynamic needs of each aspiration procedure. For example, in the example shown in FIG. 5, housing 42 of pulsator 90 defines a generally rectangular-prism shape of about 15 cm by about 20 cm by about 20 cm. In some examples, aspiration pulsator 90 weighs between about 1.3 kg and about 1.8 kg. The various embodiments of the pulsator disclosed herein can therefore be portable and connectable to a conventional (e.g., non-cyclic or constant-suction) aspiration system to add pulsed or cyclic aspiration functionality in a quick and convenient manner. This may be done, for example, in reaction to a detected need, such as following an unsuccessful attempt to employ conventional aspiration on a clot, wherein pulsed aspiration may be useful to complete the successful aspiration.

Aspiration pulsators as described herein may be formed using any suitable technique and can be used in any suitable medical procedure. FIG. 6 describes an example technique for using the aspiration systems and pulsators described herein. The technique of FIG. 6 is described with reference to the various aspects of aspiration system 10A and aspiration pulsator 20 of FIG. 1A for illustrative purposes, however, such descriptions are not intended to be limiting. The technique of FIG. 6 may be used with other aspiration systems and/or pulsators, or aspiration system 10A and/or pulsator 20 of FIG. 1A may be used using techniques other than those described with reference to FIG. 6.

Figure 6:
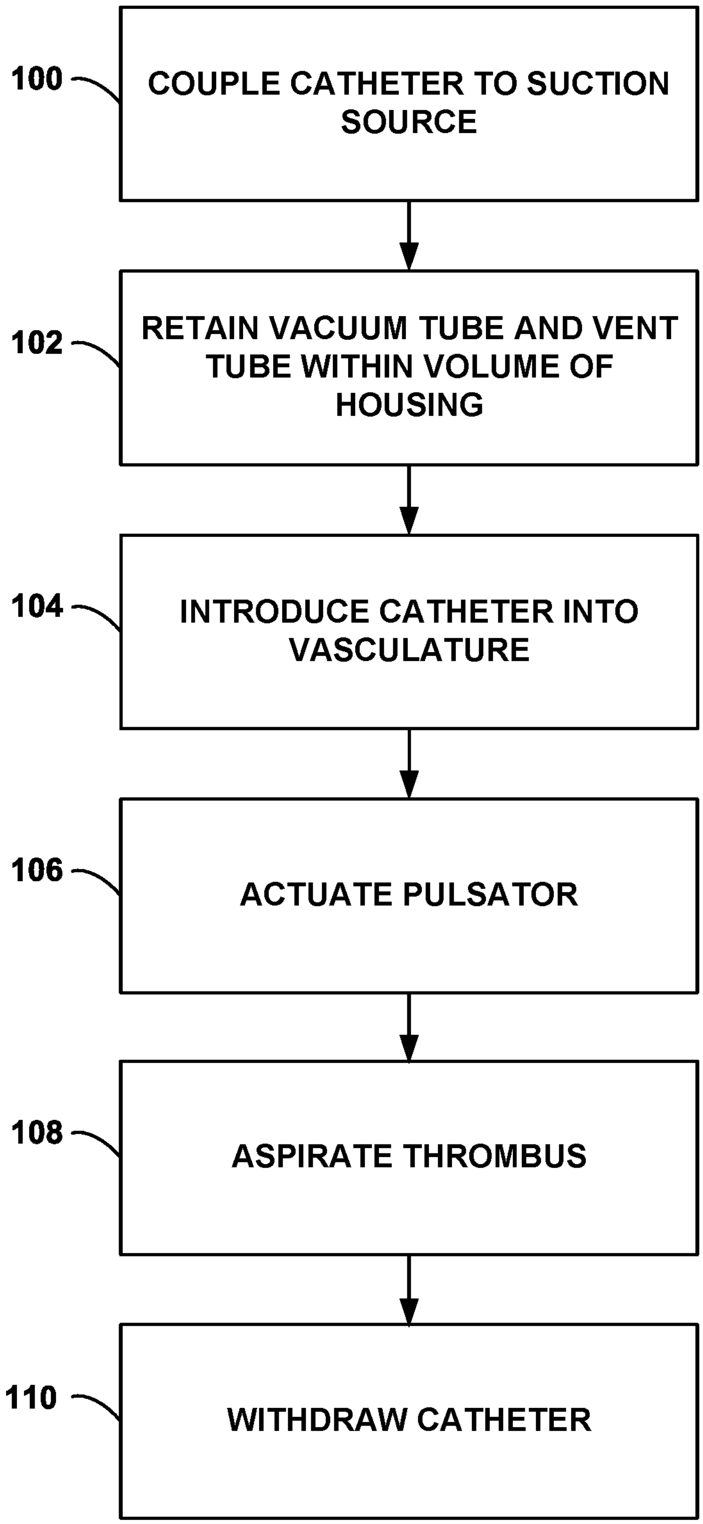
FIG. 6 is a flow diagram of an example method of using an aspiration system.

In accordance with the technique shown in FIG. 6, a clinician fluidically couples suction source 12 to the inner lumen of a catheter 18 (100). For example, the clinician may connect vacuum tube 26A to catheter 18 either directly or indirectly, e.g., via one or more additional tubes, such as that vacuum tube 26A is between suction source 12 and a lumen of catheter 18. In some examples, but not all examples, the clinician also fluidically couples catheter 18 to irrigation tube 26B (FIG. 1A) and/or a vent tube 26C (FIG. 1B). Irrigation tube 26B may couple catheter 18 to a fluid source 16, such as saline, used to flush catheter 18 during a medical procedure. In some examples, vent tube 26C fluidically couples catheter 18 to a source of ambient air 38, used to relieve the suction force and/or fluids from within the inner lumen of catheter 18.

The clinician couples aspiration pulsator 20 to vacuum tube 26A, irrigation tube 26B, and/or vent tube 26C. For example, the clinician may open a door 62 of exterior housing 42 of pulsator 20 and retain a portion of vacuum tube 26A and a portion of vent tube 26C within housing 42 (102) such that plunger 48A is aligned with vacuum tube 26A and plunger 48*b* is aligned with irrigation tube 26B and/or vent tube 26C. Thus, the clinician may position vacuum tube 26A in housing 42 such that a part of vacuum tube 26A is positioned between plunger 48A and door 62, and such that a part of irrigation tube 26B, and/or vent tube 26C is positioned between plunger 48B and door 62. In other examples, e.g., as described with reference to FIG. 4, the clinician may couple aspiration pulsator 20 to vacuum tube 26A by positioning a part of vacuum tube 26A between plunger 86A and an exterior surface of housing 42, and by positioning a part of irrigation tube 26B, and/or vent tube between plunger 86B and exterior surface of housing 42.

Prior to or after coupling catheter 18 to suction source 12, the clinician introduces catheter 18 into vasculature of a patient (104) and navigates catheter 18 to a target treatment site within a patient. In some examples, the clinician navigates catheter 18 to the target site with the aid of a guidewire, guide catheter or another guide member.

After mouth 24 of catheter 18 is positioned as desired proximate a thrombus in the vasculature, control circuitry 28, alone or based on input from a user received via user input device 76 (FIG. 3), controls suction source 12 to generate a suction force within the inner lumen of catheter 18 to aspirate the thrombus from the vasculature. In some examples, control circuitry 28, alone or based on input from a user received via user input device 76, controls pulsator 20 to convert the continuous suction force generated by suction source 12 into a periodic suction force (106). For example, control circuitry 78 may actuate a motor 64 (FIG. 2A) coupled to a rotatable cam 46. Rotatable cam 46 is configured to proximally-and-distally oscillate one or more plungers 48 configured to contact an exterior surface of the retained portion of vacuum tube 26A and/or vent tube 26C. The applied pressure from plungers 48 cause vacuum tube 26A and/or vent tube 26C to compress into a fully or partially closed configuration during which a fluid is at least partially inhibited from flowing through the inner lumen of the respective tube 26A, 26C. As the plunger oscillates to un-compress the tube 26A, 26C, the material properties of the tube cause the tube to revert back to the default, open configuration in which more fluid may flow through the respective tube compared to the compressed configuration.

In some, but not all, examples, control circuitry 28 is configured to control, via motor 64, a rotation of rotatable cam 46 (or otherwise operate (e.g., start, stop, pause, advance, retract, rotate in one direction, rotate in the opposing direction, and/or displace to or toward an endpoint in a linear or angular fashion) the actuator(s) employed to open and/or close vacuum tube 26A and/or irrigation tube 26B, as is the case with all of the embodiments of the pulsator disclosed herein) to drive a periodic opening and closing of vacuum tube 26A, irrigation tube 26B, and/or vent tube 26C between closed and open configurations according to a certain suction frequency, which may improve the outcome of the aspiration procedure. The suction frequency can be a fixed frequency over a period of time (e.g., a treatment session) or can vary over the period of time.

In some examples, control circuitry 28 determines a suction frequency for opening and compressing vacuum tube 26A and/or vent tube 26C, and then controls the rotation of rotatable cam 46 to drive the opening and compression of vacuum tube 26A, irrigation tube 26B, and/or vent tube 26C based on the determined suction frequency. The suction frequency can be, for example, the frequency with which control circuitry 28 controls motor 64 to cause rotatable cam 46 to rotate to cause plungers 48 to oscillate to cause vacuum tube 26A and/or vent tube 26C to move between a fully or partially open configuration and a less open configuration or a fully closed configuration. In some examples, the suction frequency indicates the number of times vacuum tube 26A and/or vent tube 26C are in the open configuration or the closed configuration per unit of time. For ease of description, the suction frequency is primarily referred to describe the timing with which control circuitry 28 causes vacuum tube 26A, irrigation tube 26B, and/or vent tube 26C to move between an open configuration and a closed configuration. The "open" configuration can be a fully open or a partially open configuration, and the "closed" configuration can be a less open state (e.g., a fully closed configuration or a partially closed configuration). In some examples, the suction frequency of vacuum tube 26A and/or vent tube 26C may be between about 0.5 Hz and about 30 Hz, such as about 1 Hz to about 15 Hz, or about 5 Hz to about 10 Hz. As some non-limiting examples, the suction frequency may be about 1 Hz, about 5 Hz, about 10 Hz, or about 15 Hz, according to one or more of the examples detailed further below. In some examples, 1 Hz may correspond to a cardiac cycle of some patients.

It is believed that cyclically controlling the opening and compression of vacuum tube 26A and/or vent tube 26C according to a particular suction frequency may more quickly and/or more effectively remove a thrombus from a blood vessel of a patient by varying an amount of suction force applied to the thrombus. Control circuitry 28 can cause rotatable cam 46 to cause vacuum tube 26A and/or vent tube 26C to move between the open and closed configurations according to the suction frequency while suction source 12 generates a steady-state, constant or substantially constant suction force (referred to herein as non-cyclic aspiration). In any of these examples, the suction frequency can be fixed or control circuitry 28 can change the suction frequency over time (e.g., during an aspiration procedure).

Control circuitry 28 can determine the suction frequency using any suitable technique. As some non-limiting examples, control circuitry 28 may determine the suction frequency based on user input, based on a value stored in memory 30 or a memory of another device, based on a natural frequency (e.g., a resonant frequency) of a thrombus, and/or based on a cardiac cycle of a patient.

In some examples, control circuitry 28 determines the suction frequency by at least receiving user input indicating the suction frequency via user-input device 76 (FIG. 3) or another user input mechanism. For example, user-input device 76 or another user input mechanism can include a button, a keypad, a touchscreen, a microphone configured to receive voice commands, or the like, through which the user can input a selected suction frequency. In some examples, control circuitry 28 is configured to receive user input selecting a suction frequency from a plurality of predetermined suction frequencies (e.g., stored by memory 30 of aspiration system 10A or a memory of another device). In these examples, user-input device 76 may include a display, a rotating dial, or the like that presents the predetermined suction frequencies to the user, from which the user can select one or more suction frequencies for controlling the rotation of rotatable cam 46. In addition to or instead of determining the suction frequency based on user input, in some examples, control circuitry 28 is configured to receive user input indicating a desired suction frequency value.

In some examples, sensing circuitry 32 is configured to detect a natural frequency (e.g., a resonant frequency) of a clot within the patient's vasculature. As one example, the natural frequency of the clot may be between about 5 Hz and 10 Hz. In such examples, control circuitry 28 may determine the suction frequency of vacuum tube 26A, irrigation tube 26B, and/or vent tube 26C based the signal generated by sensing circuitry 32 and indicative of the natural frequency of the clot. The contact between a thrombus and the vasculature in which the thrombus is positioned may include certain properties such that, when the suction force with which aspiration system 10A aspirates the thrombus is periodically modified, via rotatable cam 46, according to a particular frequency, the thrombus may more effectively become dislodged and aspirated into the inner lumen of catheter 18.

In other examples, the suction frequency is predetermined. In these examples, control circuitry 28 may determine the suction frequency by retrieving the predetermined suction frequency from memory 30 or a memory of another device and without any user input indicating the suction frequency.

In addition to or instead of any of the other previous examples for determining a suction frequency, in some examples, control circuitry 28 is configured to determine the suction frequency based on a cardiac cycle of a patient. It is believed that coordinating the extent to which vacuum tube 26A and/or vent tube 26C are compressed with the cardiac cycle may affect the amount of suction force applied to thrombus proximate mouth 24. For example, synchronizing the compression, or the attainment of the closed state of, vacuum tube 26A and/or vent tube 26C with certain parts of the cardiac cycle (e.g., diastole or systole) may more quickly and more effectively remove a thrombus from a blood vessel of a patient than applying a continuous or steady suction force, or other forms of cyclic aspiration.

In some examples, control circuitry 28 may first determine (e.g., measure, detect, or receive from another device) a cardiac cycle of the patient, and then determine the suction frequency of vacuum tube 26A and/or vent tube 26C based on the cardiac cycle. As one example, the cardiac cycle of the patient at one point in time may be on the order of 60 beats per minute (bpm). In some such examples, control circuitry 28 may select the suction frequency to be on the order of about 1 Hz, and/or synchronize the aspiration pulses (e.g., those periods of time when vacuum tube 26A is completely, nearly completely or partially open) with a particular portion of the cardiac cycle, e.g. systole or diastole, or any other suitable portion. Such synchronization can incorporate a time lag or a time lead between the relevant portion of the cardiac cycle, and the aspiration pulses, to counter-act delays that may result from the configuration of the aspiration system.

Control circuitry 28 of aspiration system 10A can determine a cardiac cycle (e.g., the current phase of a cardiac cycle) using any suitable technique, e.g., based on a physiological signal sensed by sensing circuitry 32. The signal can include, for example, one or more of an ECG, an EGM, a photoplethysmogram (PPG), a heart sound phonocardiogram, or a blood pressure signal. In addition to or instead of receiving physiological signals from sensing circuitry 32, in some examples, control circuitry 28 may receive signals from another device that determines the current part of the cardiac cycle and transmits the determined part of the cardiac cycle to control circuitry 28.

In some examples, the technique of FIG. 6 further includes aspirating the thrombus (104) and removing catheter 18 from the vasculature of the patient once the procedure is complete (106).

The techniques described in this disclosure, including those attributed to control circuitry 28, and sensing circuitry 32, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry 28, and sensing circuitry 32, instead of or in addition to the partially or wholly digital hardware and/or software described herein. Accordingly, analog or digital hardware may be employed, or a combination of the two. Whether implemented in digital or analog form, or in a combination of the two, control circuitry 28 can comprise a timing circuit configured to command the rotation of rotatable cam 46 to cause the periodic compression of vacuum tube 26A, irrigation tube 26B, and/or vent tube 26C according to a predetermined frequency, the application of a suction force (via, e.g., command of pulsator 20 in fluid communication with suction source 12) in synchrony with the patient's cardiac cycle or another predetermined frequency, or any combination thereof.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

The following clauses provide some examples of the disclosure. The examples described herein may be combined in any permutation or combination.

Clause 1: In some examples, a device is configured to convert a constant suction force to a periodic suction force, the device including: a housing configured to receive a portion of a vacuum tube and a portion of a vent tube; a first plunger; a second plunger; and a rotatable cam configured to cause the first plunger to periodically compress the vacuum tube and to cause the second plunger to periodically compress the vent tube.

Clause 2: In some examples of the device of clause 1, the rotatable cam includes a cylindrical body defining a circumferential groove configured to receive a first portion of the first plunger and a first portion of the second plunger, wherein rotation of the cylindrical body causes a second portion of the first plunger to periodically compress the vacuum tube and causes a second portion of the second plunger to periodically compress the vent tube.

Clause 3: In some examples of the device of clause 1, the rotatable cam includes a cylindrical body defining a first circumferential groove configured to receive a first portion of the first plunger and a second circumferential groove configured to receive a first portion of the second plunger, wherein rotation of the cylindrical body causes a second portion of the first plunger to periodically compress the vacuum tube and causes a second portion of the second plunger to periodically compress the vent tube.

Clause 4: In some examples of the device of clause 3, the first groove and the second groove are substantially helical grooves that extend both longitudinally and circumferentially with respect to a longitudinal axis of the cylindrical body.

Clause 5: In some examples of the device of clause 3, the cylindrical body includes a first cylindrical body including the first groove and a second cylindrical body including the second groove.

Clause 6: In some examples of the device of clause 5, the first cylindrical body and the second cylindrical body are rotatable with respect to each other to enable modification of a circumferential orientation of the first groove relative to the second groove, wherein an overlap duration of compression of the vacuum tube and compression of the vent tube is based on the circumferential orientation of the first groove relative to the second groove.

Clause 7: In some examples of the device of clause 3, the first groove includes a first proximal groove portion and a first distal groove portion; the second groove includes a second proximal groove portion and a second distal groove portion; the first proximal groove portion biases the first plunger away from the vacuum tube; the first distal groove portion biases the first plunger to hold the vacuum tube closed; the second proximal groove portion biases the second plunger away from the vent tube; and the second distal groove portion biases the second plunger to hold the vent tube closed.

Clause 8: In some examples of the device of any of clauses 1-7, the first plunger and the second plunger are linear, the rotatable cam is configured to rotate to cause the first plunger to periodically compress the vacuum tube away from the cam, and the cam is configured to rotate to cause the second plunger to periodically compress the vent tube away from the rotatable cam.

Clause 9: In some examples of the device of any of clause 1-7, the first plunger and the second plunger are hook-shaped, the rotatable cam is configured to rotate to cause the first plunger to periodically compress the vacuum tube toward the cam, and the cam is configured to rotate to cause the second plunger to periodically compress the vent tube toward the cam.

Clause 10: In some examples of the device of clause 9, the device further includes a clamping spring disposed between the rotatable cam and an interior surface of the housing, the clamping spring configured to bias the first plunger toward the vacuum tube and to bias the second plunger toward the vent tube.

Clause 11: In some examples of the device of any of clauses 1-10, the housing includes: a user-interface control panel; and control circuitry configured to control a speed of rotation of the rotatable cam, wherein the control circuitry is configured to receive user input via the user-interface control panel and control the speed of rotation of the rotatable cam based on the user input.

Clause 12: In some examples of the device of clause 11, the control circuitry is configured to pause a rotation of the rotatable cam in response to the user input.

Clause 13: In some examples of the device of clause 12, in response to receiving the user input indicative of a request to pause the rotation of the rotatable cam, the control circuitry is configured to select a time at which to pause the rotation of the rotatable cam such that the vacuum tube or the vent tube remains compressed or uncompressed while the rotation of the rotatable cam is paused.

Clause 14: In some examples of the device of any of clauses 1-13, the housing includes control circuitry configured to control a speed of rotation of the rotatable cam, wherein the control circuitry is configured to cause the rotatable cam to rotate at a frequency of between about 1.5 Hz and about 15 Hz.

Clause 15: In some examples of the device of clause 14, the control circuitry is configured to cause the rotatable cam to rotate at a frequency of between about 6 Hz and about 12 Hz.

Clause 16: In some examples of the device of any of clauses 1-15, the housing defines a rectangular prism of about 15 cm by about 20 cm by about 20 cm.

Clause 17: In some examples of the device of any of clauses 1-16, the device weighs about 1.3 kg to about 1.8 kg.

Clause 18: In some examples of the device of any of clauses 1-17, the housing defines an interior space and includes a door configured to retain the vacuum tube and the vent tube within the interior space.

Clause 19: In some examples of the device of any of clauses 1-18, the device further includes a motor mechanically coupled to the rotatable cam; and a removable battery configured to power the motor to rotate the cam.

Clause 20: In some examples of the device of clause 19, the battery is configured to attach to an exterior surface of the housing.

Clause 21: In some examples of the device of any of clauses 1-20, the vacuum tube and the vent tube are configured to fluidically coupled to a catheter, and rotation of the rotatable cam is configured to establish the periodic suction force within a lumen of the catheter via the vacuum tube and the vent tube.

Clause 22: In some examples, a system includes: a vacuum source; a vacuum tube coupled to the vacuum source; a vent tube; and a device including: a housing configured to receive a portion of the vacuum tube and a portion of the vent tube; a first plunger; a second plunger; a rotatable cam configured to rotate to cause the first plunger to periodically compress the vacuum tube and to cause the second plunger to periodically compress the vent tube; and a motor configured to rotate the rotatable cam; and control circuitry configured to configured to control the motor to control the rotation of the rotatable cam.

Clause 23: In some examples of the system of clause 22, the system further includes an aspiration catheter coupled to the vacuum tube and to the vent tube, wherein the vacuum tube is configured to connect a lumen of the catheter to the vacuum source to establish a suction force in the lumen of the catheter.

Clause 24: In some examples of the system of clause 22, the housing includes a user-interface control panel; the control circuitry is configured to control a speed of rotation of the rotatable cam, and the control circuitry is configured to receive user input via the user-interface control panel and control the speed of rotation of the rotatable cam based on the user input.

Clause 25: In some examples of the system of clause 22, the vent tube is configured to connect a lumen of the catheter to a saline source or a vent.

Clause 26: In some examples, an aspiration system includes: a sterile field; an aspiration tube located in the sterile field; a motorized pulsator located in the sterile field and coupled to the aspiration tube; wherein the pulsator is operable to open and close the aspiration tube to flow of liquid through the tube.

Clause 27: In some examples of the aspiration system of clause 26, the pulsator includes: a motor; and a first actuator operable by the motor and positioned to open or close the aspiration tube to flow of fluid through the tube.

Clause 28: In some examples of the aspiration system of clause 26 or clause 27, the pulsator includes a battery configured to power the motor.

Clause 29: In some examples of the aspiration system of any of clauses 26-28, the pulsator is positioned entirely in the sterile field.

Clause 30: In some examples of the aspiration system of any of clauses 26-29, the pulsator is sterile.

Clause 31: In some examples of the aspiration system of clause 26, the system further includes an aspiration catheter connected to the aspiration tube, wherein the aspiration catheter is configured for insertion into a blood vessel of a patient.

Clause 32: In some examples of the aspiration system of clause 31, the system further includes a vent tube located in the sterile field, wherein the aspiration catheter is connected to the aspiration tube and the vent tube.

Clause 33: In some examples of the aspiration system of any of clauses 26-32, the system further includes a vent tube located in the sterile field, the pulsator is operable to open or close the vent tube to flow of fluid through the tube.

Clause 34: In some examples of the aspiration system of clause 31, the pulsator includes a motor and first and second actuators positioned to open or close the aspiration tube and the vent tube, respectively, to flow of fluid through the respective tube.

Clause 35: In some examples of the aspiration system of clause 31, the first and second actuators are operable to close and open the aspiration tube and the vent tube via external compression of the tubes, and release of such compression.

Clause 36: In some examples of the aspiration system of clause 34 or clause 35, the first and second actuators are each configured to interact solely with an exterior of the aspiration tube and an exterior of the vent tube, respectively.

Clause 37: In some examples of the aspiration system of clause 27, the actuator is operable to close and open the aspiration tube via external compression of the tube, and release of such compression.

Clause 38: In some examples of the aspiration system of clause 37, the actuator is configured to interact solely with an exterior of the aspiration tube.

Clause 39: In some examples of the aspiration system of any of clauses 34-36, the pulsator further includes a receptacle configured to receive the aspiration tube and the vent tube, the receptacle including: a first chamber for receiving the aspiration tube, the first chamber being within an actuation range of the first actuator; and a second chamber for receiving the vent tube, the second chamber being within an actuation range of the second actuator.

Clause 40: In some examples, a method includes facilitating the addition of pulsed aspiration capability to an aspiration system having an aspiration tube, the method including: providing a sterilizable, motorized pulsator; enabling the coupling of the pulsator to the aspiration tube by providing, as a component of the pulsator, a receptacle configured to receive the aspiration tube in a manner that enables the opening and closing, via the pulsator, of the aspiration tube to flow of fluid through the tube.

Clause 41: In some examples of the method of clause 40, the method further includes enabling the opening and closing, via the pulsator, of the aspiration tube to flow of fluid through the aspiration tube via interaction of the pulsator solely with the exterior of the aspiration tube.

Clause 42: In some examples of the method of clause 40 or clause 41, the aspiration system further includes a vent tube, and the method further includes enabling the coupling of the pulsator to the vent tube by configuring the receptacle to receive the vent tube in a manner that enables the opening and closing, via the pulsator, of the vent tube to flow of fluid through the vent tube.

Clause 43: In some examples of the method of clause 42, the method further includes enabling the opening and closing, via the pulsator, of the vent tube to flow of fluid through the vent tube via interaction of the pulsator solely with the exterior of the vent tube.

Clause 44: In some examples of the method of any of clauses 40-43, the pulsator includes a battery configured to power the motor of the pulsator.

Clause 45: In some examples of the method of clause 44, the pulsator is sterile.

Clause 46: In some examples of the method of clause 40, the method further includes enabling the opening and closing, via the pulsator, of the aspiration tube to flow of fluid through the aspiration tube via external compression of the aspiration tube, and release of such compression.

Clause 47: In some examples of the method of clause 42, the method further includes enabling the opening and closing, via the pulsator, of the vent tube to flow of fluid through the vent tube via external compression of the vent tube, and release of such compression.

Clause 48: In some examples of the method of clause 42, the pulsator further includes a first actuator configured to open and close the aspiration tube, and a second actuator configured to open and close the vent tube.

Clause 49: In some examples of the method of clause 48, the receptacle includes: a first chamber for receiving the aspiration tube, the first chamber being within an actuation range of the first actuator; and a second chamber for receiving the vent tube, the second chamber being within an actuation range of the second actuator.

Clause 50: In some examples of the method of clause 48, engagement of the pulsator with the aspiration system places the aspiration tube within an actuation range of the first actuator, and placed the vent tube within an actuation range of the second actuator.

Clause 51: In some examples of the method of clause 40, the aspiration system further includes an aspiration catheter connected to the aspiration tube.

Clause 52: In some examples of the method of clause 51, the aspiration system further includes a vent tube, and the aspiration catheter is connected to the vent tube.

Clause 53: In some examples, a method includes, in an aspiration system having an aspiration tube located in a sterile field, adding the capability of pulsed aspiration by placing in the sterile field a sterile motorized pulsator and connecting the pulsator to the aspiration tube to enable opening and closing the tube to fluid flow via the pulsator.

Various aspects of the disclosure have been described. These and other aspects are within the scope of the following claims.

What is claimed is:

1. A device configured to convert a constant suction force to a periodic suction force, the device comprising:

a housing configured to receive a portion of a vacuum tube and a portion of a vent tube;

a rotatable cam comprising an exterior surface that forms a single body, wherein the single body of the rotatable cam comprises a cylindrical body defining a circumferential groove on the exterior surface;

a first plunger coupled to the single body of the rotatable cam; and a second plunger coupled to the same single body of the rotatable cam as the first plunger, wherein the rotatable cam is configured to cause the first plunger to periodically compress the vacuum tube and to cause the second plunger to periodically compress the vent tube, and wherein the circumferential groove is configured to receive a first portion of the first plunger and a first portion of the second plunger.

2. The device of claim 1, wherein rotation of the cylindrical body causes a second portion of the first plunger to periodically compress the vacuum tube and causes a second portion of the second plunger to periodically compress the vent tube.

3. The device of claim 1, wherein the first plunger and the second plunger are linear, and wherein the rotatable cam is configured to rotate to cause the first plunger to periodically compress the vacuum tube away from the cam, and wherein the cam is configured to rotate to cause the second plunger to periodically compress the vent tube away from the rotatable cam.

4. The device of claim 1, wherein the first plunger and the second plunger are hook-shaped, and wherein the rotatable cam is configured to rotate to cause the first plunger to periodically compress the vacuum tube toward the cam, and wherein the cam is configured to rotate to cause the second plunger to periodically compress the vent tube toward the cam.

5. The device of claim 1, wherein the housing comprises:

a user-interface control panel; and control circuitry configured to control a speed of rotation of the rotatable cam, wherein the control circuitry is configured to receive user input via the user-interface control panel and control the speed of rotation of the rotatable cam based on the user input.

6. The device of claim 5, wherein, in response to receiving user input indicative of a request to pause the rotation of the rotatable cam, the control circuitry is configured to select a time at which to pause the rotation of the rotatable cam such that the vacuum tube or the vent tube remains compressed or uncompressed while the rotation of the rotatable cam is paused.

7. The device of claim 1, wherein the housing comprises control circuitry configured to control a speed of rotation of the rotatable cam, wherein the control circuitry is configured to cause the rotatable cam to rotate at a frequency of between about 1.5 Hz and about 15 Hz.

8. The device of claim 1, wherein the device further comprises:

a motor mechanically coupled to the rotatable cam; and a removable battery configured to power the motor to rotate the cam.

9. The device of claim 1, wherein the vacuum tube and the vent tube are configured to fluidically couple to a catheter, and wherein rotation of the rotatable cam is configured to establish the periodic suction force within a lumen of the catheter.

10. The device of claim 1, wherein the rotatable cam has only the single body, the first and second plungers being coupled to the single body.

11. The device of claim 1, wherein the single body of the rotatable cam defines a helical groove configured to receive at least one of the first plunger or the second plunger.

12. A system comprising:

a vacuum source;

the vacuum tube configured to be coupled to the vacuum source;

the vent tube;

the device of claim 1;

a motor configured to rotate the rotatable cam of the device of claim 1; and control circuitry configured to control the motor to control the rotation of the rotatable cam.

13. The system of claim 12, further comprising an aspiration catheter fluidically coupled to the vacuum tube and to the vent tube, wherein the vacuum tube is configured to connect a lumen of the catheter to the vacuum source to establish a suction force in the lumen of the catheter.

14. A device configured to convert a constant suction force to a periodic suction force, the device comprising:

a housing configured to receive a portion of a vacuum tube and a portion of a vent tube;

a first plunger;

a second plunger; and a rotatable cam coupled to both the first and second plungers, wherein the rotatable cam comprises a groove configured to receive a first portion of the first plunger and a first portion of the second plunger, and wherein rotation of the rotatable cam causes the first plunger to periodically compress the vacuum tube and causes the second plunger to periodically compress the vent tube.

15. The device of claim 14, wherein the rotatable cam comprises a cylindrical body defining the groove, wherein rotation of the cylindrical body causes a second portion of the first plunger to periodically compress the vacuum tube and causes a second portion of the second plunger to periodically compress the vent tube.

* * * * *